United States Patent [19]

Handa et al.

[11] Patent Number: 4,543,273
[45] Date of Patent: Sep. 24, 1985

[54] CARBON MONOXIDE SENSING ELEMENT AND METHOD OF MAKING SAME

[75] Inventors: Takashi Handa, Kamakura; Yoshiaki Okayama, Yamato, both of Japan

[73] Assignee: Nohmi Bosai Kogyo Co., Ltd., Tokyo, Japan

[21] Appl. No.: 563,928

[22] Filed: Dec. 21, 1983

[30] Foreign Application Priority Data

Dec. 25, 1982 [JP] Japan ................................ 57-226510

[51] Int. Cl.$^4$ ............................................. B05D 5/12
[52] U.S. Cl. ................................ 427/126.3; 427/376.2; 427/376.3; 427/377; 422/94; 73/23
[58] Field of Search ............... 427/126.3, 376.2, 376.3, 427/377; 422/94; 73/23

[56] References Cited

U.S. PATENT DOCUMENTS

| 3,864,628 | 2/1975 | Klass et al. | 73/23 |
| 3,901,067 | 8/1975 | Boardman et al. | 73/23 |
| 4,033,169 | 7/1977 | Fujishiro | 73/23 |
| 4,251,225 | 2/1981 | Handa | 73/23 |

Primary Examiner—Richard Bueker
Attorney, Agent, or Firm—Wenderoth, Lind & Ponack

[57] ABSTRACT

An element for selectively sensing carbon monoxide which is capable of sensing a lower concentration of CO in a quicker response time at ordinary temperatures without the need of heating the element with better SN and low temperature dependence.

3 Claims, 2 Drawing Figures

CARBON MONOXIDE SENSING ELEMENT AND METHOD OF MAKING SAME

BACKGROUND OF THE INVENTION

The present invention relates to a carbon monoxide sensing element and more particularly it relates to a carbon monoxide sensing element capable of sensing selectively lower concentrations of carbon monoxide within a quicker response time with better SN and temperature-resistance variation ratios than the prior art. The present invention also relates to a method of making such an element.

Heretofore there have been many reports on the study of CO gas sensing elements and they have also been described in various patent documents. Of such patent literature the following examples can be listed;

Japanese Patent Publication No. 45-38200 (1970) discloses a warning apparatus for reducing gases such as $H_2O$, $C_2H_2$ comprising a reduction type semi-conductor such as ZnO or $SnO_2$ as a sensing element, the sensing ability of which is connected through an amplifier or directly to a warning display and the sensing element is heated to eliminate the effects of humidity on the response of said element and to effect the rapid adsorption/desorption of the reducing gas on said element. This apparatus operates for example, in excess of 500° K. for any organic gas such as $C_3H_6$, and in excess of 420° K. for $H_2$, CO or city gas containing same.

Japanese Patent Publication No. 47-38840 (1972) discloses a gas responsive element comprising a reduction type semi-conductor metal oxide base material, a catalyst selected from at least one of a group consisting of Pa, Ag, Fe, Co, Ni, Mo and Cu with the prerequisite that said catalyst differs from said base material, and a restoring agent selected from a group consisting of MgO, PbO and CaO. As the semi-conductor material metal oxide semi-conductors such as ZnO, SnO, $Fe_2O_3$, CdO, $V_2O_5$, $TiO_2$ and $TaO_2$ are named. This publication also describes in the sole example that the heating of said gas responsive element is necessary for actual use. The example illustrates application of this element to city gas.

Japanese Patent Publication No. 53-23195 (1978) describes an apparatus for sensing the concentration of carbon monoxide comprising a sensing element composed of metal oxide semi-conductor material, said sensing element being produced by adding to stannic oxide or a salt of tin decomposing into stannic oxide upon being fired, at least one selected from salts of platinum and platinum black and firing the resultant composite, and means for changing the temperature of said element, the detection of the concentration of carbon monoxide being effected by the particular temperature at which an abrupt dramatic change of electric resistance in said element occurs. This sensing element selectively responds to carbon monoxide in a gaseous atmosphere, but it also requires heating means upon measurement.

U.S. Pat. No. 4,000,089 describes an element which can detect selectively carbon monoxide from other reducing gases contained in air. The element has a composition comprising stannic oxide as a basic material, platinum black as a catalyst and if necessary, clay, ferric oxide or glassy substances as a calcining agent. FIG. 4 shows a graphic chart in which if the temperature is fixed at 60° C. the sudden change of electric resistance value occurs at a carbon monoxide content of 500 ppm in air and it is insensitive to contents below 500 ppm carbon monoxide. Further this patent shows the electric resistance at 25° C. of reducing gases including CO of 1000 ppm in air.

Japanese Patent Laid Open 56-49950 (1981) discloses a sensing element comprising a semi-conductor wafer composed of a base of stannic oxide to which at least a predetermined amount of Pt is carried and having a platinum pin electrode in pin contact with the semi-conductor wafer as one electrode. This laid open publication also discloses the optional doping of a trace amount of antimony for stabilizing the temperature properties.

Further, in Japanese Patent Laid Open No. 53-143298 which partly corresponds to U.S. Pat. No. 4,251,225, a $SnO_2$-$Sb_2O_3$-Pt type sensing element for carbon monoxide composed of stannic oxide ($SnO_2$), antimony trioxide ($Sb_2O_3$) and platinum (Pt) which has a suppressed temperature dependence without impairing the selectivity for carbon monoxide (CO).

This $SnO_2$-$Sb_2O_3$-Pt type sensing element for carbon monoxide requires no heater for heating the element, but has a disadvantage in that low concentrations of CO gas cannot be detected.

However, such gas detectors have many disadvantages such as low selectivity for CO detection, the need for heating the gas sensing element, the high temperature dependence and the like.

The present inventor carried out various tests in view of the above point and succeeded in achieving a CO gas sensing element which by using antimony oxychloride (SbOCl) in place of the compositional constituent $Sb_2O_3$ can detect lower concentrations of CO gas, has superior response to gas and also excellent thermal characteristics in comparison to the prior $SnO_2$-$Sb_2O_3$-Pt type gas sensing elements and further it does not require a heater.

SUMMARY OF THE PRESENT INVENTION

The present invention relates to a carbon monoxide sensing element prepared by mixing stannic oxide, antimony oxychloride and platinum in ratios of Sb/Sn equalling 2 to 8 mol %, a Pt/Sn ratio of 2 to 10 mol % and calcining said mixture at a temperature of 600° C. to 850° C.

The present invention also relates to a method of making an element for sensing carbon monoxide comprising a first process of adding and thoroughly dispersing an aqueous chloroplatinic acid solution to the stannic oxide in the range of Pt/Sn=2-10 mol % whereupon the mixture is frozen and dried in a vacuum, a second process of adding and mixing antimony oxychloride to the product made in the first process in the range of Sb/Sn=2-8 mol %, a third process of adding an organic solvent to the product made in the second process and applying and drying the resulting paste on an insulator to which electrodes are attached and a fourth process of calcining the element made in the third process in an air or oxidizing antimony gas atmosphere at 600 to 850° C.

DETAILED EXPLANATION OF THE INVENTION

The invention of a CO gas sensing element will be explained below by use of experimental examples.

EXAMPLE 1

An aqueous chloroplatinic acid solution ($H_2PtCl_6$) is added to $SnO_2$ in a ratio of Pt/Sn=4 mol % and thoroughly dispersed by ultrasonic waves. After this aqueous dispersion is quick frozen at $-40°$ C., it is set in a vacuum freeze drier and dried. Next SbOCl is added to this freeze dried product in a ratio of Sb/Sn=4 mol % and mixed together in a mortar for 30 minutes. This mixed product is then converted into a paste-like material by the addition of isopropyl alcohol and is then coated on an alumina porcelain tube to which electrodes are attached and dried naturally. Next this element is put into a quartz tube with an air temperature set at $700°$ C.$\pm 5°$ C. and calcined for 30 minutes to produce a gas sensing element. The gas sensing element is thereupon aged for 24 hours in an air atmosphere at $250°$ C.$\pm 50°$ C.

A gas sensing element made in the above fashion was placed in a $25°$ C. air atmosphere and then exposed to respective 100 ppm concentrations of CO gas, hydrogen gas ($H_2$), ethyl alcohol gas (EtOH) and city gas in air, the electric resistance values were measured and the resulting ratios of electric resistance value ($R_o$) in air to the electric resistance values ($R_g$) in each gas are shown in the $R_o/R_g$ column of Table 1.

TABLE 1

|  |  |  | $R_o/R_g$ |
|---|---|---|---|
| CO | gas | 100 ppm | 20 |
| $H_2$ | gas | 100 ppm | 1.21 |
| EtOH | gas | 100 ppm | 3.98 |
| City | gas | 100 ppm | 2.25 |

Figure 1:
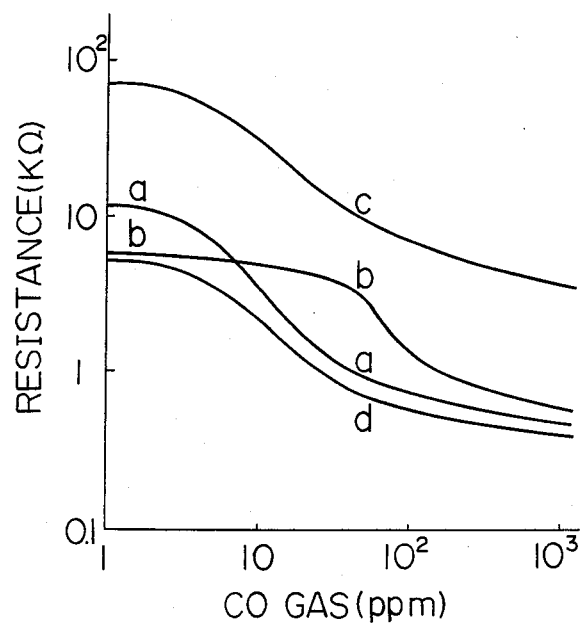
FIG. 1 and FIG. 2 are graphs showing the characteristics of CO gas concentration in relation to changes in electric resistance of a CO gas sensing element made according to the two examples, where a,c-g are the different characteristics of the sensing elements according to this invention and b is the characteristics of a sensing element of the prior art.

Further the characteristics of changes in electric resistance towards concentrations of CO gas in air of a gas sensing element having an Ro of 12.5 K$\Omega$ and an Rg of 0.7 K$\Omega$ in a 100 ppm CO gas atmosphere selected from among 16 gas sensing elements made according to Example 1 were determined and are shown by (a) in FIG. 1. Further, the characteristics of the $SnO_2$ - $Sb_2O_3$ - Pt type gas sensing element of the prior art are as shown by (b) in FIG. 1. Said gas sensing element employed in the determination of electric resistance change characteristics as a function of CO concentration in air has an electric resistance of 0.7 K$\Omega$ in 100 ppm CO concentration in air and has a resistance of 12.5 K$\Omega$ in air at $25°$ C.

Next, in order to derive the effective compositional ratio as well as the range of calcining temperatures for this gas sensing element a number of gas sensing elements were made with the above method while changing the compositional ratio of Pt/Sn to 1,2,4,6,8 and 10 mol %, Sb/Sn to 1,2,4,6,8 and 10 mol %, and the calcining temperature to $550°$, $600°$, $650°$, $700°$, $750°$, $800°$, $850°$ and $900°$ C. Then the value of electric resistance in air ($R_o$) in a CO gas free $25°$ C. atmosphere and the value of electric resistance in air containing 100 ppm CO gas ($R_{co}$) as well as the values of electric resistance when in air containing 100 ppm CO gas at $-10°$ C. ($R_{-10}$) and at $50°$ C. ($R_{50}$) of the gas sensing element were measured and the results of the measurements were used to come up with an $R_o/R_{co}$ or SN ratio and an $R_{-10}/R_{50}$ or electric resistance variation ratio as a function of temperature. Also the response time of each gas sensing element when exposed to atmospheres which are free of CO gas and those with 100 ppm of CO gas. Representative examples of these compositional ratios, calcining temperatures as well as the measuring results are listed in Table 2.

TABLE 2

| Pt/Sn Mol % | Sb/Sn Mol % | Calcining Temp. °C. | $R_o/R_{co}$ (25° C.) | $R_{-10}/R_{50}$ | Response Time (Sec) |
|---|---|---|---|---|---|
| 4 | 4 | 550 | 27 | 12.0 | 51 |
| 4 | 4 | 600 | 25 | 5.2 | 34 |
| 4 | 4 | 650 | 22 | 3.7 | 23 |
| 4 | 4 | 700 | 20 | 2.5 | 20 |
| 4 | 4 | 750 | 20 | 3.0 | 22 |
| 4 | 4 | 800 | 18 | 4.5 | 34 |
| 4 | 4 | 850 | 10 | 5.2 | 71 |
| 4 | 4 | 900 | 6 | 7.3 | 120 |
| 4 | 1 | 700 | 8 | 7.0 | 89 |
| 4 | 2 | 700 | 15 | 4.5 | 62 |
| 4 | 6 | 700 | 20 | 2.5 | 21 |
| 4 | 8 | 700 | 18 | 2.7 | 26 |
| 4 | 10 | 700 | 6 | 6.0 | 100 |
| 1 | 4 | 700 | 9 | 6.0 | 94 |
| 2 | 4 | 700 | 12 | 4.0 | 46 |
| 6 | 4 | 700 | 17 | 3.0 | 30 |
| 8 | 4 | 700 | 15 | 4.3 | 35 |
| 10 | 4 | 700 | 15 | 5.0 | 37 |
| 1 | 1 | 700 | 7 | 7.0 | 120 |
| 1 | 10 | 700 | 3 | 2.5 | 120 |
| 2 | 2 | 700 | 12 | 4.4 | 80 |
| 2 | 8 | 700 | 14 | 4.2 | 75 |
| 8 | 2 | 700 | 15 | 4.3 | 80 |
| 8 | 8 | 700 | 10 | 4.0 | 60 |
| 10 | 1 | 700 | 14 | 8.0 | 50 |
| 10 | 10 | 700 | 2 | 1.5 | 30 |

Of the results of the measurement of the electric resistance variation characteristics to changes in CO gas concentrations in these gas sensing elements, the characteristics of a gas sensing element calcined at $700°$ C. of Pt/Sn=2 mol %, Sb/Sn=2 mol %, are shown as (c) and the characteristics of one of Pt/Sn=8 mol %, Sb/Sn=8 mol % and a calcining temperature of $700°$ C. are shown as (d) in FIG. 1 respectively. Further, the measured average result of the $R_o/R_{co}$, $R_{-10}/R_{50}$, and response time of a prior $SnO_2$ - $Sb_2O_3$ - Pt type gas sensing element is $R_o/R_{co}=5$, $R_{-10}/R_{50}=5.0$ and a response time of 80 seconds.

From the above results it can be seen that if $SnO_2$, SbOCl and $H_2PtCl_6$ are mixed in compositional ratios of Pt/Sn=2 to 10 mol %, Sb/Sn=2 to 8 mol % and are calcined in an air atmosphere of $600°$ to $850°$ C., a gas sensing element can be obtained that has high selectivity towards CO gas, and in comparison to the prior $SnO_2$ -$Sb_2O_3$ - Pt type gas sensing elements not only can detect lower concentrations of CO gas with favorable SN as well as electric resistance-temperature variation ratios, but which also responds quickly to CO gas.

EXAMPLE 2

An aqueous chloroplatinic acid solution ($H_2PtCl_6$) is added to $SnO_2$ in a ratio of Pt/Sn=4 mol % and thoroughly dispersed by ultrasonic waves. After this aqueous dispersion is quick frozen at $-40°$ C., it is set in a vacuum freeze drier and dried. Next SbOCl is added to this freeze dried product in a ratio of Sb/Sn=4 mol % and mixed together in a mortar for 30 minutes. This mixed product is then converted into a paste-like material by the addition of isopropyl alcohol and is then coated on an alumina porcelain tube to which electrodes are attached and air dried. On the one hand an alumina boat with 2.5 mg of SbOCl in the bottom of the boat is sealed for 30 minutes inside a 40mm inside diameter quartz tube the length of which is to be inserted into an electric furnace being 50 cm thereof and set at 700 ±5° C. making an oxidizing antimony gas atmosphere within the quartz tube. The above air dried element is then sealed within this quartz tube with an oxidizing antimony gas atmosphere set at 700°±5° C. and calcined for 30 minutes to produce a gas sensing element. The gas sensing element is thereupon aged for 24 hours in an air atmosphere at 250° C. ±50° C.

A gas sensing element made in the above fashion was placed in a 25° C. air atmosphere and then exposed to respective 100ppm concentrations of CO gas, hydrogen gas ($H_2$), ethyl alcohol gas (EtOH) and city gas in air, the electric resistance values were measured and the resulting ratios of the electric resistance value ($R_o$) in air to the electric resistance values ($R_g$) in each gas are shown in the $R_o/R_g$ column of Table 3.

TABLE 3

|  |  |  | $R_o/R_g$ |
|---|---|---|---|
| CO | gas | 100 ppm | 21 |
| $H_2$ | gas | 100 ppm | 1.94 |
| EtOH | gas | 100 ppm | 5.12 |
| City | gas | 100 ppm | 4.48 |

Figure 2:
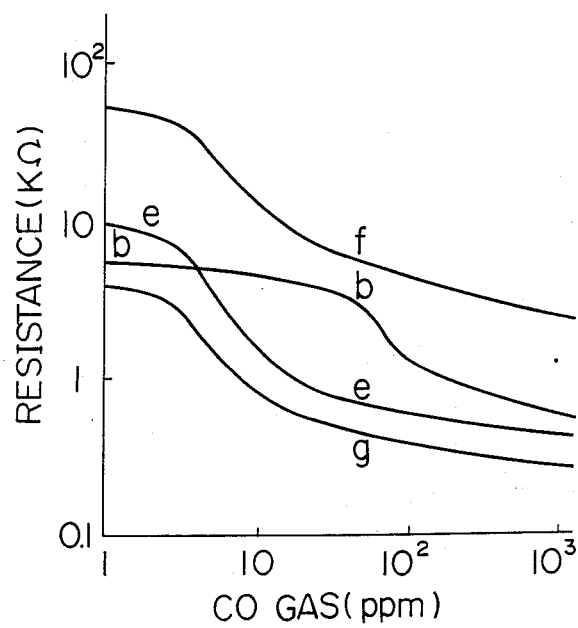

Also the characteristics of changes in electric resistance towards concentrations of CO gas in air of a gas sensing element having an $R_o$ of 0.55 KΩ in a 100 ppm CO atmosphere selected from 16 gas sensing elements made according to example 2 were determined and are shown by (e) in FIG. 2. Further, the characteristics of the $SnO_2$-$Sb_2O_3$-Pt type gas sensing element of the prior art are as shown by (b) in FIG. 2.

Next gas sensing elements were made using the above method and varying the amount of SbOCl for making the oxidizing antimony gas atmosphere within the quartz tube to 0.25, 0.5, 1.0, 2.5, 5.0 and 7.5 mg. Then the value of electric resistance in air ($R_o$) in a CO gas free atmosphere and the value of electric resistance in 100 ppm CO gas containing air ($R_{co}$) at 25° C. as well as the value of electric resistance when in a 100 ppm CO gas atmosphere at −10° C. ($R_{-10}$) and at 50° C. ($R_{50}$) of the gas sensing element were respectively measured and the results of the measurements were used to come up with an $R_o/R_{co}$ or SN ratio and an $R_{-10}/R_{50}$ or temperature-electric resistance variation ratio. Also the response time of each gas sensing element when exposed to 25° C. atmospheres and those which are free of CO gas to those with 100 ppm of CO gas. The results are listed in Table 4.

TABLE 4

| SBOCL (mg) | $R_o/R_{co}$ | $R_{-10}/R_{50}$ | Response Time (Sec) at 25° C. |
|---|---|---|---|
| 0.25 | 3.2 | 6.7 | 160 |
| 0.5 | 5.9 | 4.9 | 77 |
| 1.0 | 11.2 | 3.2 | 25 |
| 2.5 | 21 | 2.0 | 22 |
| 5.0 | 27.3 | 4.7 | 80 |
| 7.5 | 16.7 | 10.5 | 240 |

Gas sensing elements were also made in the same manner as above using $Sb_2O_3$ instead of SbOCl for making the oxidizing antimony gas atmosphere within the quartz tube by changing the amount of $Sb_2O_3$ to 0.25, 0.5, 1.0, 2.5, 5.0 and 7.5 mg and these gas sensing elements thus prepared were used for determining the $R_o$, $R_{co}$, $R_{-10}$, $R_{50}$ and $R_{-10}/R_{50}$, $R_o/R_{co}$ ratios as well as for measuring the response time. These results are shown in Table 5.

TABLE 5

| $Sb_2O_3$ (mg) | $R_o/R_{co}$ | $R_{-10}/R_{50}$ | Response Time (Sec) |
|---|---|---|---|
| 0.25 | 3.1 | 7.9 | 155 |
| 0.5 | 5.7 | 4.7 | 72 |
| 1.0 | 8.3 | 3.6 | 26 |
| 2.5 | 10.5 | 2.4 | 19 |
| 5.0 | 23.6 | 4.3 | 71 |
| 7.5 | 9.6 | 12.0 | 190 |

Further, a number of gas sensing elements were made with the above method while changing the compositional ratio of Pt/Sn to 1,2,4,6,8 and 10 mol %, Sb/Sn to 1,2,4,6,8 and 10 mol %, and the calcining temperature to 550°, 600°, 650°, 700°, 750°, 800°, 850° and 900° C. Moreover the amount of SbOCl for making the oxidizing antimony gas atmosphere within the quartz tube was set at 2.5 mg and the elements were made using the same respective calcining temperatures and these gas sensing elements were used for determining $R_o$, $R_{co}$, $R_{-10}$, $R_{50}$ in the same manner as above in order to get $R_{-10}/R_{50}$, $R_o/R_{co}$ ratios, as well as for measuring the response time. These compositional ratios and calcining temperatures as well as representative examples of those results are shown in Table 6.

TABLE 6

| Pt/Sn Mol % | Sb/Sn Mol % | Calcining Temp. °C. | $R_o/R_{co}$ (25° C.) | $R_{-10}/R_{50}$ | Response Time (Sec) |
|---|---|---|---|---|---|
| 4 | 4 | 550 | 28 | 11.2 | 76 |
| 4 | 4 | 600 | 26 | 4.6 | 35 |
| 4 | 4 | 650 | 28 | 3.3 | 28 |
| 4 | 4 | 700 | 21 | 2.0 | 22 |
| 4 | 4 | 750 | 14 | 2.7 | 28 |
| 4 | 4 | 800 | 12 | 3.9 | 39 |
| 4 | 4 | 850 | 7 | 4.9 | 76 |
| 4 | 4 | 900 | 6 | 7.9 | 105 |
| 4 | 1 | 700 | 11 | 6.5 | 92 |
| 4 | 2 | 700 | 13 | 4.6 | 67 |
| 4 | 6 | 700 | 19 | 2.1 | 21 |
| 4 | 8 | 700 | 15 | 2.1 | 26 |
| 4 | 10 | 700 | 8 | 4.9 | 91 |
| 1 | 4 | 700 | 11 | 5.7 | 82 |
| 2 | 4 | 700 | 16 | 4.2 | 51 |
| 6 | 4 | 700 | 16 | 2.8 | 30 |
| 8 | 4 | 700 | 12 | 3.1 | 31 |
| 10 | 4 | 700 | 13 | 4.3 | 34 |
| 1 | 1 | 700 | 8 | 7.1 | 98 |
| 1 | 10 | 700 | 4 | 1.8 | 130 |
| 2 | 2 | 700 | 14 | 4.7 | 60 |
| 2 | 8 | 700 | 13 | 4.1 | 70 |
| 8 | 2 | 700 | 14 | 4.9 | 50 |
| 8 | 8 | 700 | 11 | 3.2 | 53 |
| 10 | 1 | 700 | 18 | 7.7 | 61 |
| 10 | 10 | 700 | 3 | 1.7 | 35 |

Of the results of the measurement of the electric resistance variation characteristics as a function of the change in CO gas concentrations of these gas sensing elements, the characteristics of a gas sensing element calcined at 700° C. in an oxidizing antimony gas atmosphere resulting from 2.5 mg of SbOCl at a Pt/Sn ratio of 2 mol %, and a Sb/Sn ratio of 2 mol % are shown as (f) and the characteristics of one of Pt/Sn=8 mol %, Sb/Sn=8 mol % are shown as (g) in FIG. 2 respectively.

From the above results it can be seen that if $SnO_2$, SbOCl and $H_2PtCl_6$ are mixed in compositional ratios of Pt/Sn=2 to 10 mol %, Sb/Sn=2 to 8 mol % and the resulting mixture is calcined in a 600° to 850° C. oxidizing antimony gas atmosphere obtained as a result of calcining 0.5 to 5 mg of SbOCl or $Sb_2O_3$ (amounting to $Sb_2O_3$ being $2\times10^{-9}$ to $3\times10^{-8}$ mol/$cm^3$), whereby a gas sensing element can be obtained that has high selectivity towards CO gas, and in comparison to the prior $SnO_2$ - $Sb_2O_3$ - Pt type gas sensing elements not only can detect lower concentrations of CO gas with favorable SN as well as electric resistance-temperature variation ratios, but which also responds quickly to CO gas.

As solvents to make the mixture into a paste-like material such organic solvents as 25 wt % -terpineol, 72 wt % butyl-carbitol acetate, 3 wt % ethyl cellulose etc. may be used besides isopropyl alcohol, and as the base upon which the paste-like material is coated any flat or tubular insulating body besides a porcelain tube which can withstand calcining may be used and also a thermostatic chamber etc. may be used for the drying of the elements. Also, solid or gaseous antimony trichloride ($SbCl_3$), antimony hydride gas (SbH) or the like may be used in making the oxidizing antimony gas atmosphere within the quartz tube.

According to this invention as explained above, there is provided a $SnO_2$ - SbOCl - Pt type carbon monoxide gas sensing element and a method of manufacturing said element, said element having a high selectivity towards CO gas as well as being able to detect lower concentrations of CO gas and further, because of its favorable SN as well as temperature-electric resistance variation ratios can respond quickly.

Furthermore, the reason the sensing element of this invention in comparison to the sensing elements of the prior art can detect lower concentrations of carbon monoxide gas with favorable SN as well as temperature-electric resistance variation ratios and with quicker response times can be attributed to the selection of antimony oxychloride as one of the compositional elements of the sensing element, the antimony oxychloride decomposing in a wide temperature range of 245° to 575° C. when being calcined thereby generating an antimony oxide gas, the antimony oxide gas then depositing on the platinum from low temperatures when the platinum, which can be added in the form of a salt or an acid, is reduced to platinum black thereby preventing the formation of large metal clumps of platinum at high temperatures thus creating a large surface area of active metallic platinum.

What we claim is:

1. A method of making a carbon monoxide sensing element comprising a first process of adding and thoroughly dispersing an aqueous chloroplatinic acid solution to stannic oxide in the range of Pt/Sn=2-10 mol % whereupon the mixture is quick frozen and dried in a vacuum, a second process of adding and mixing antimony oxychloride to the product made in the first process in the range of Sb/Sn=2-8 mol %, a third process of adding an organic solvent to the product made in the second process and applying and drying the resulting paste on an insulator to which electrodes are attached and a fourth process of calcining the element made in the third process in an air atmosphere at 600° to 850° C.

2. A method of making a carbon monoxide sensing element comprising a first process of adding and thoroughly dispersing an aqueous chloroplatinic acid solution to stannic oxide in the range of Pt/Sn=2-10 mol % whereupon the mixture is quick frozen and dried in a vacuum, a second process of adding and mixing antimony oxychloride to the product made in the first process in the range of Sb/Sn=2-8 mol %, a third process of adding an organic solvent to the product made in the second process and applying and drying the resulting paste on an insulator to which an electrode is attached and a fourth process of calcining the element made in the third process in an atmosphere of previously prepared oxidizing antimony gas at 600° to 850° C.

3. A method of making a carbon monoxide sensing element according to claim 2 wherein the oxidizing antimony gas atmosphere is prepared by firing a $2\times10^{-9}$ to $3\times10^{-8}$ mol/$cm^3$ quantity of antimony compound calculated as a mol quantity of antimony trioxide.

* * * * *